(12) United States Patent
Sarraj Asil

(10) Patent No.: US 10,517,581 B2
(45) Date of Patent: Dec. 31, 2019

(54) CARDIAC SURGERY RETRACTOR

(71) Applicant: Anas Sarraj Asil, Madrid (ES)

(72) Inventor: Anas Sarraj Asil, Madrid (ES)

( * ) Notice: Subject to any disclaimer, the term of this patent is extended or adjusted under 35 U.S.C. 154(b) by 149 days.

(21) Appl. No.: 15/739,728

(22) PCT Filed: Apr. 11, 2016

(86) PCT No.: PCT/ES2016/070248
§ 371 (c)(1),
(2) Date: Dec. 24, 2017

(87) PCT Pub. No.: WO2017/013283
PCT Pub. Date: Jan. 26, 2017

(65) Prior Publication Data
US 2018/0185017 A1     Jul. 5, 2018

(30) Foreign Application Priority Data

Jul. 20, 2015  (ES) .................................. 201531065

(51) Int. Cl.
*A61B 17/02*     (2006.01)
*A61B 17/00*     (2006.01)

(52) U.S. Cl.
CPC ...... *A61B 17/0218* (2013.01); *A61B 17/0206* (2013.01); *A61B 2017/00243* (2013.01);
(Continued)

(58) Field of Classification Search
CPC ............ A61B 17/0293; A61B 17/0206; A61B 17/0218; A61B 2017/00946;
(Continued)

(56) References Cited

U.S. PATENT DOCUMENTS 6,019,722 A    2/2000  Spence et al.
6,036,641 A    3/2000  Taylor et al.
(Continued)

FOREIGN PATENT DOCUMENTS

DE    102012219727    4/2014
EP         0532710    3/1993
(Continued)

OTHER PUBLICATIONS

International Search Report and the Written Opinion dated Jul. 29, 2016 From the International Searching Authority Re. Application No. PCT/ES2016/070248. (12 Pages).

*Primary Examiner* — David W Bates
*Assistant Examiner* — Marcela I Shirsat

(57) ABSTRACT

Cardiac surgery retractor which comprises a baseband formed by a first base and a second base, mutually arranged in a perpendicular manner and forming a cross-section of the baseband in the shape of an L, the second base being planar and the first base having a curved geometry; the baseband incorporating a fin formed by a profile with a cross-section also in the shape of an L and the fin being articulated at the second base of the baseband, at a lateral edge of the second base contiguous to the contact thereof with the first base of the same baseband; such that in one position of the joint of the fin, one of the sides of the L profile forming the fin is the continuation of the same second base and the other side of the same L profile of the fin is the continuation of the first base.

9 Claims, 15 Drawing Sheets

(52) U.S. Cl.
CPC ............... *A61B 2017/00946* (2013.01); *A61B 2017/0237* (2013.01); *A61B 2017/0243* (2013.01)

(58) Field of Classification Search
CPC .... A61B 2017/0237; A61B 2017/0243; A61B 2017/00243
USPC ........ 600/204, 206, 210–211, 213–216, 219, 600/235
See application file for complete search history.

(56) References Cited

U.S. PATENT DOCUMENTS

| | | | | |
|---|---|---|---|---|
| 2004/0122293 | A1* | 6/2004 | Douglas | A61B 1/32 600/212 |
| 2007/0129608 | A1 | 6/2007 | Sandhu | |
| 2008/0108877 | A1* | 5/2008 | Bayat | A61B 17/02 600/214 |
| 2009/0299147 | A1* | 12/2009 | Epstein | A61B 17/0218 600/213 |
| 2011/0137128 | A1* | 6/2011 | Poo | A61B 17/02 600/206 |
| 2015/0245828 | A1* | 9/2015 | Harari | A61B 17/0218 600/204 |
| 2017/0065266 | A1* | 3/2017 | Landanger | A61B 17/02 |

FOREIGN PATENT DOCUMENTS

| | | |
|---|---|---|
| KR | 10-2011-0033641 | 3/2011 |
| WO | WO 2006/110733 | 10/2006 |
| WO | WO 2007/075903 | 7/2007 |

\* cited by examiner

CARDIAC SURGERY RETRACTOR

RELATED APPLICATIONS

This application is a National Phase of PCT Patent Application No. PCT/ES2016/070248 having International filing date of Apr. 11, 2016, which claims the benefit of priority of Spanish Patent Application No. P201531065 filed on Jul. 20, 2015. The contents of the above applications are all incorporated by reference as if fully set forth herein in their entirety.

FIELD AND BACKGROUND OF THE INVENTION

The object of the present patent application is to register a cardiac surgery retractor which incorporates notable innovations and advantages with respect to the techniques used hitherto.

More specifically, the invention proposes the development of a cardiac surgery retractor, which due to the particular arrangement thereof, facilitates the work of the surgeon during the cardiac surgery as well as improves the final results thereof.

The surgical operations in cardiovascular surgery are known in the current state of the art.

Some documents known in the current state of the art are, for example, US20040122293A1, US20110137128A1, US20150245828A1, US20080108877A1, US20090299147A1, US20150282795A1 or US20170065266A1.

The repair or replacement of the mitral, aortic or tricuspid valves is very common in these operations, whereby it is essential for the surgeons to have a good field of work and work space.

In the specific case of cardiac surgery of the mitral valve, good exposure of the mitral valve and its ring is essential for the surgeon.

In conventional surgery known in the state of the art, the sternum is opened with a retractor and then the surgical operation is carried out with the patient connected to an extracorporeal circulation machine to oxygenate the blood and pump it back to the body and using the so-called Cosgrove retractor, which has a sternal separator and two or three valves which are fixed to the sternal separator, in order to thus simultaneously carry out anterior traction and caudal traction with respect to the body.

Minimally invasive surgery (MIS) is also known in the state of the art. The use thereof is increasingly more common in theatres and it is also starting to be applied little by little in heart operations where, in addition to reducing the scarring, it also serves for reducing the recovery time of the patients.

MIS allows complete sternotomy to be reduced or even avoided which is how the complete cutting and separation of the sternum is known, being the common incision in heart operations. In this way, instead of carrying out an incision of between 20 and 25 centimeters, an incision of barely seven centimeters is sufficient.

Once the incision has been carried out, endoscopic cameras can also be used which help to improve vision.

Potentially, MIS can be applied to between 50 and 60 percent of heart surgeries since it is possible to carry out valve replacements and even treat some tumors or congenic cardiopathies.

This is an alternative surgery with huge benefits, both aesthetic and for reducing the recovery time which, in turn, involves the patient getting back to work sooner.

In minimally invasive mitral surgery, only an anterior traction valve is used. There is a metal arm articulated with the valve for separating the wall of the left auricle in the caudal direction.

The present invention helps to facilitate said surgical operations for the surgeon as well as to improve the final result thereof, both in conventional cardiac surgery and MIS, since it provides the surgeon with significantly improved working conditions in relation to the known state of the art.

SUMMARY OF THE INVENTION

The present invention has been developed with the aim of providing a cardiac surgery retractor, enabled for the preferred use thereof in minimally invasive surgery and for the use thereof with a diaphragm which is essentially characterized by the fact that it comprises a baseband formed by a larger base and a smaller base, the larger base and the smaller base mutually arranged in a perpendicular manner and forming a cross-section of the baseband in the shape of an L, the smaller base being planar and the larger base having a curved geometry with a convex physiognomy in relation to the contact thereof with the smaller base and the baseband therefore having an intersection line between the larger base and the smaller base with a geometric shape of a circumferential arc or similar; the baseband incorporating a fin formed by a profile with a cross-section also in the shape of an L and the fin being articulated at the smaller base of the baseband, at a lateral edge of the smaller base contiguous to the contact thereof with the larger base of the same baseband; such that in one position of the joint of the fin, one of the sides of the L profile forming the fin is the continuation of the same smaller planar base of the baseband and the other side of the same L profile of the fin is the continuation of the curved geometry of the larger base of the baseband and the line of the vertex of the L profile is the continuation of the geometric shape of the intersection line between the larger base and the smaller base of the baseband; and in another position of the joint of the fin, the planar side of the L profile of the fin is positioned on the smaller base of the baseband; the surface of the convex face of the larger base and the curved side of the L profile of the fin both being rough; and the end of the larger base opposite the intersection line with the smaller base incorporates two arms articulated with respect to the larger base itself which, in one position of said joint, are positioned on the face of the larger base which corresponds to the concave part of the same larger base and in another position of the same joint are arranged extended and with an orientation perpendicular to the larger base itself in a direction opposite the position of the smaller base; the edge of the smaller base, which is in a position opposite the intersection line with the larger base, incorporating a tubular extension towards the exterior of the smaller base itself.

Alternatively, in the cardiac surgery retractor, the tubular extension is enabled for carrying an accessory carrying a diaphragm.

Additionally, the cardiac surgery retractor incorporates fixing means for positioning the planar side of the L profile of the fin on the smaller base of the baseband.

Alternatively, in the cardiac surgery retractor, the axial axis of the tubular extension is contained in the same plane as the smaller base.

Alternatively, in the cardiac surgery retractor, the axial axis of the tubular extension is contained in a plane oblique with respect to the smaller base.

More specifically, in the cardiac surgery retractor, the oblique plane, which contains the axial axis of the tubular extension, forms an angle of 45° with respect to the smaller base.

Preferably, in the cardiac surgery retractor, the fixing means comprise a hole in the planar side of the L profile of the fin which is complementary to an awl positioned on the smaller base of the baseband.

Additionally, in the cardiac surgery retractor, the arms are malleable.

Preferably, in the cardiac surgery retractor, the tubular extension is enabled for incorporating a handle inserted coaxially to the axial axis thereof.

Owing to the present invention, surgical operations can be facilitated for the surgeon as well as the final result thereof being improved, both in conventional cardiac surgery and in MIS since it provides the surgeon with significantly improved working conditions in relation to the known state of the art.

Other characteristics and advantages of the cardiac surgery retractor will be evident from the description of a preferred, but not exclusive embodiment which is illustrated in an exemplary, non-limiting manner in the drawings which are enclosed, in which:

DESCRIPTION OF A PREFERRED EMBODIMENT

The cardiac surgery retractor of the present invention is enabled for the preferred use thereof in minimally invasive surgery as well as for incorporating a diaphragm in the use thereof.

Figure 1:
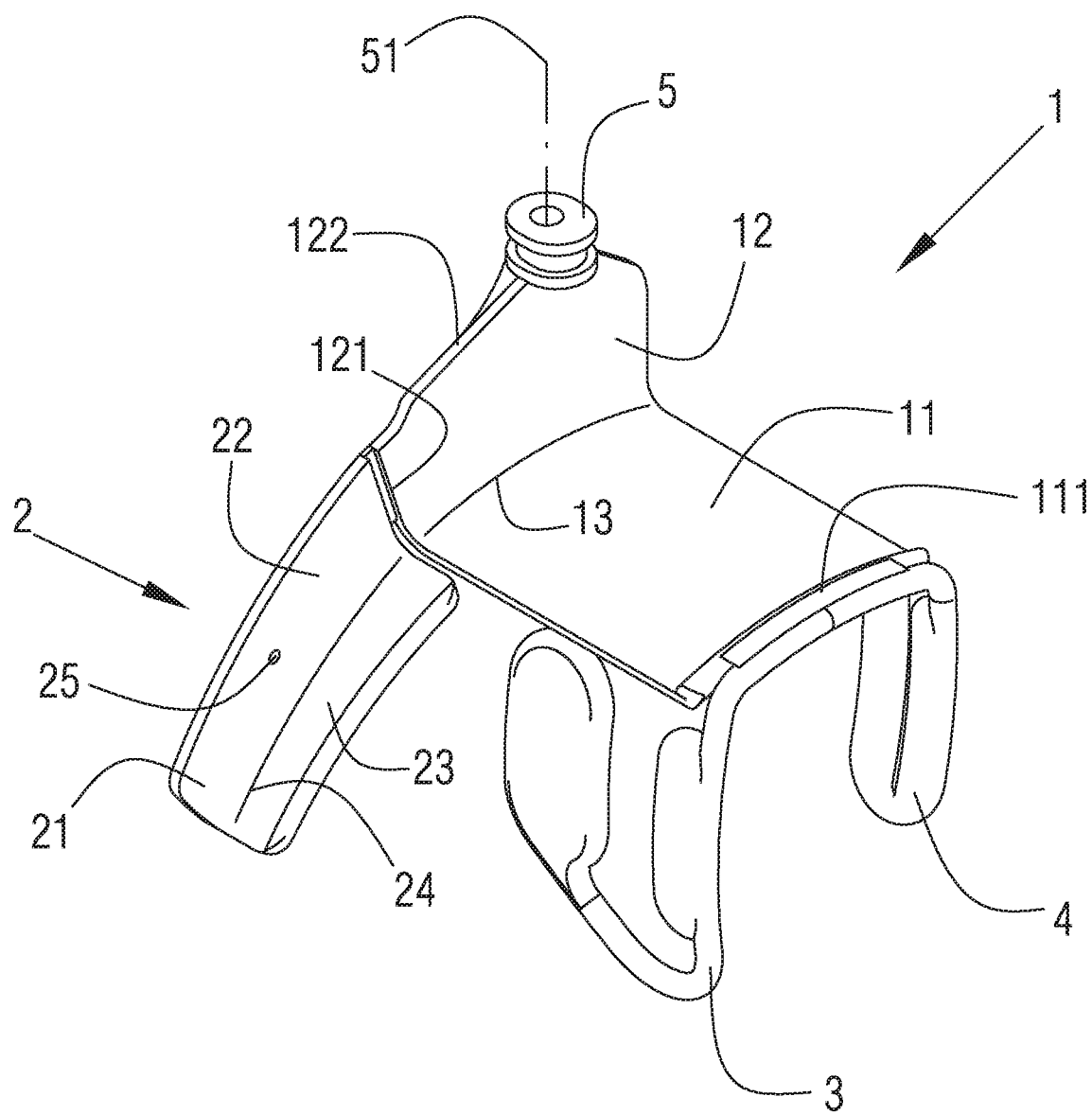
FIGS. 1, 2 and 3 are perspective and schematic views of a preferred embodiment of the cardiac surgery retractor of the present invention with the joint thereof unfolded.
Figure 2:
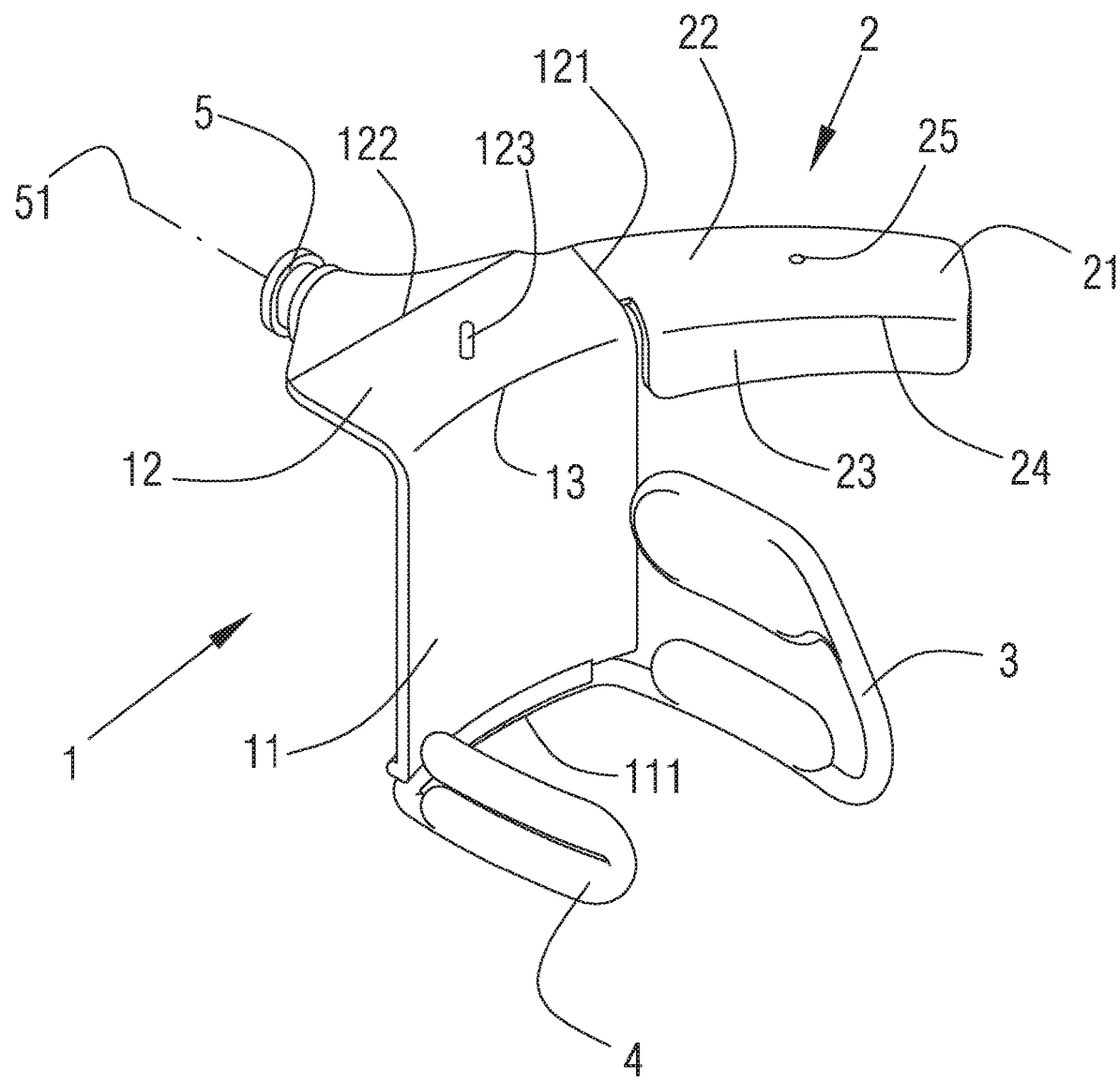
Figure 3:
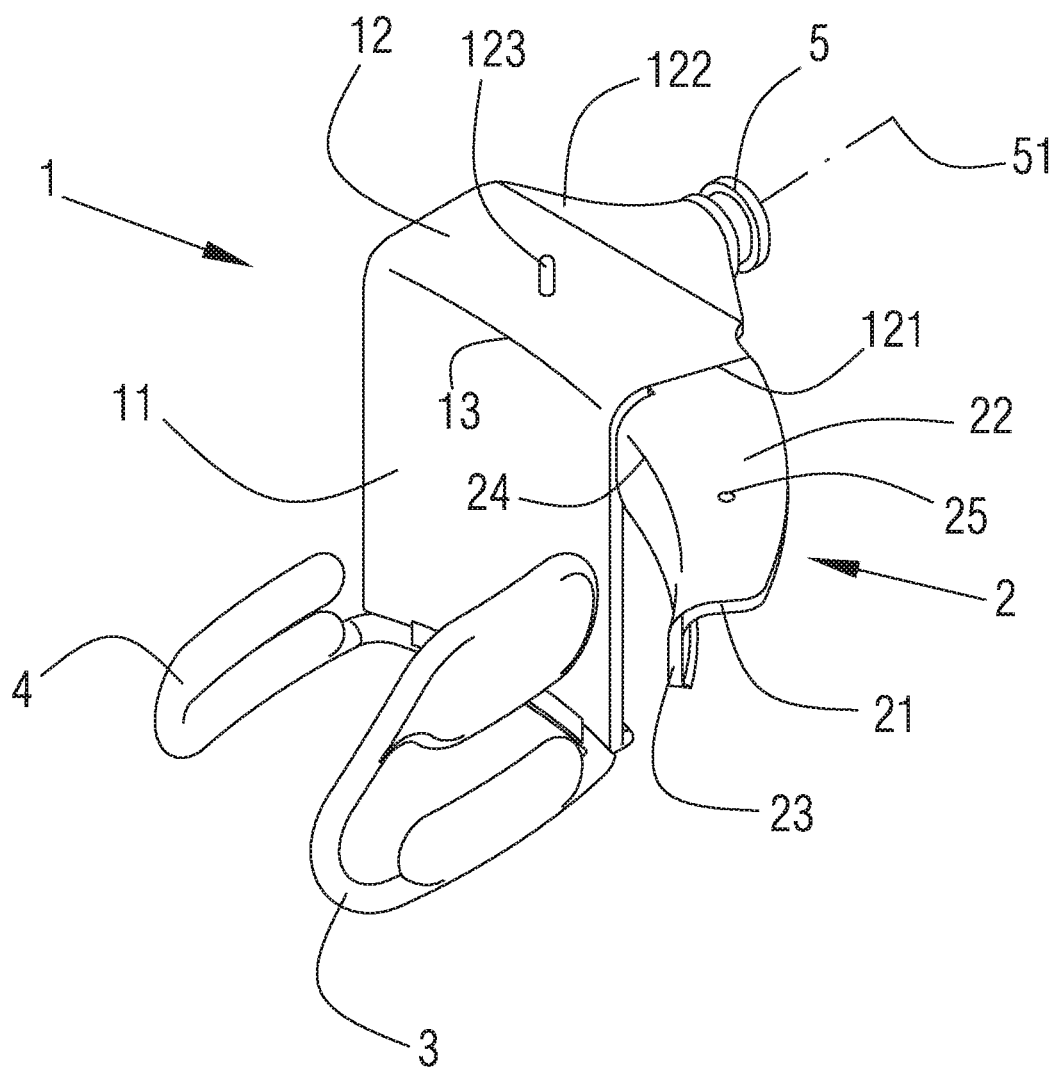

As is schematically shown in FIGS. 1, 2 and 3 from different perspectives, the cardiac surgery retractor of the invention comprises a baseband 1 formed by a larger or first base 11 and a smaller or second base 12. The larger base 11 and the smaller base 12 are mutually arranged in a perpendicular manner and forming a cross-section of the baseband 1 in the shape of an L.

The smaller base 12 is planar. In contrast, the larger base 11 has a curved geometry with a convex surface or physiognomy in relation to the contact thereof with the smaller base 12.

More specifically, in this preferred embodiment, the larger base 11 has a curved geometry similar to a portion of the lateral surface of a cylinder with a base parallel to the smaller base 12 and generatix also perpendicular to the smaller base 12.

According to the geometric arrangement described, the intersection line 13 between the larger base 11 and the smaller base 12 has a geometric shape of a circumferential arc.

In the cardiac surgery retractor of the invention, the baseband 1 incorporates a fin 2. Said fin 2 is formed by a profile 21 with a cross-section also in the shape of an L. In addition, the fin 2 is articulated at the smaller base 12 of the base band 1.

More specifically, the fin 2 is articulated at a lateral edge 121 of the smaller base 12 which is contiguous to the contact of the smaller base 12 with the larger base 11 of the same baseband 1.

The joint of the fin 2 with the smaller base 12 is implemented such that in one position of the same joint, one of the sides 22 of the L profile 21 forming the fin 2 is the continuation of the same smaller planar base 12 of the baseband 1 and the other side 23 of the same L profile 21 of the fin 2 is the continuation of the described curved geometry of the larger base 11 of the baseband 1. According to which, the line of the vertex 24 of the L profile 21 of the fin 2 is the continuation of the intersection line 13 between the larger base 11 and the smaller base 12 of the baseband 1.

The surface of the convex face of the larger base 11 and the side 23 of the curved geometry of the L profile 21 of the fin 2 are both rough.

Figure 4:
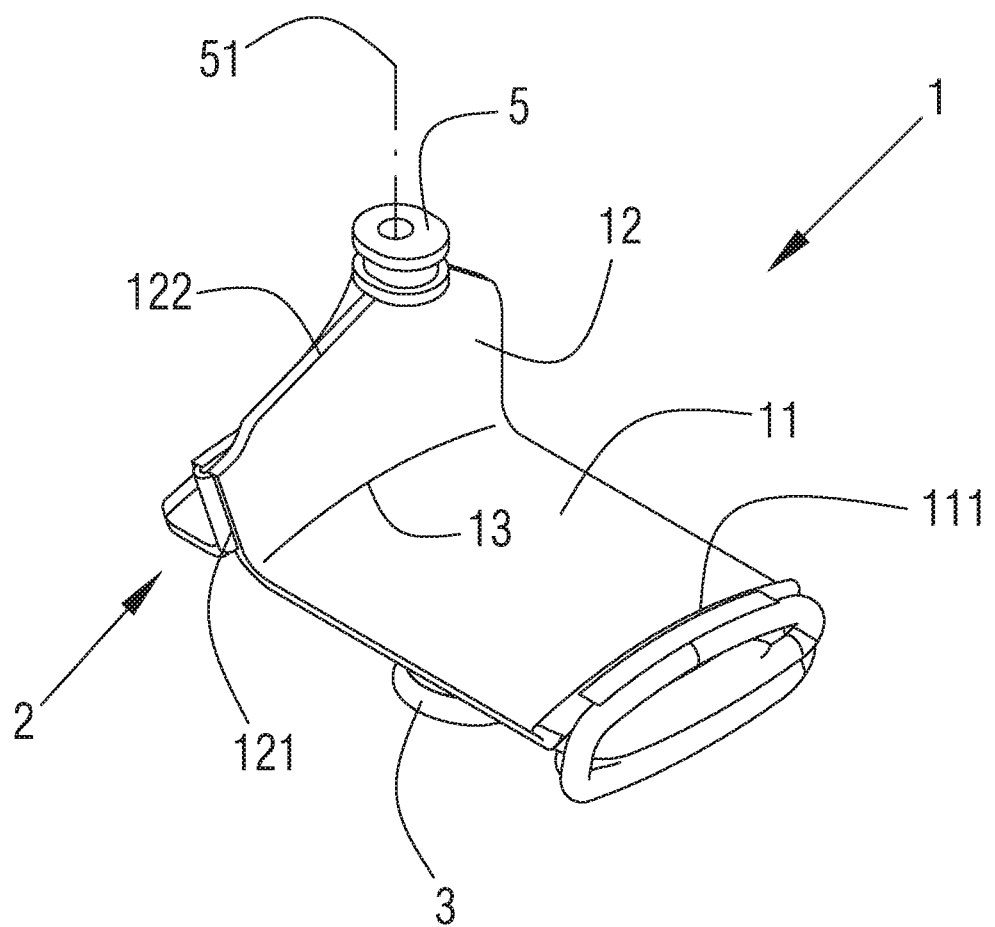
FIGS. 4, 5 and 6 are perspective and schematic views of a preferred embodiment of the cardiac surgery retractor of the present invention of FIGS. 1 to 3, but with the joint thereof folded.
Figure 5:
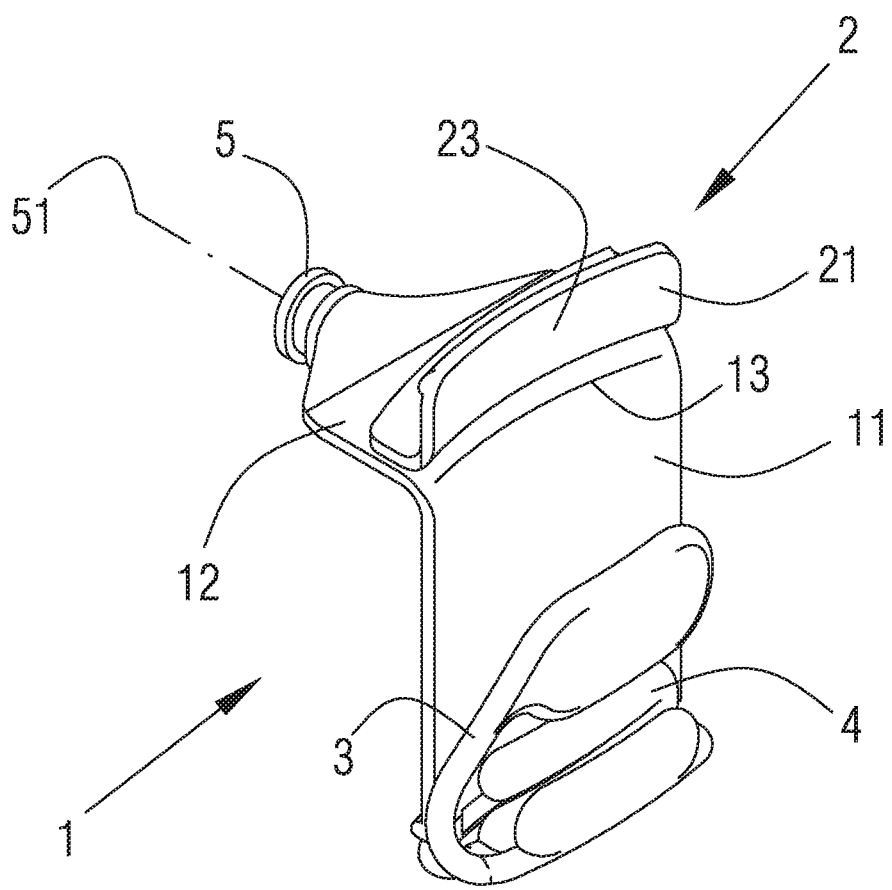
Figure 6:
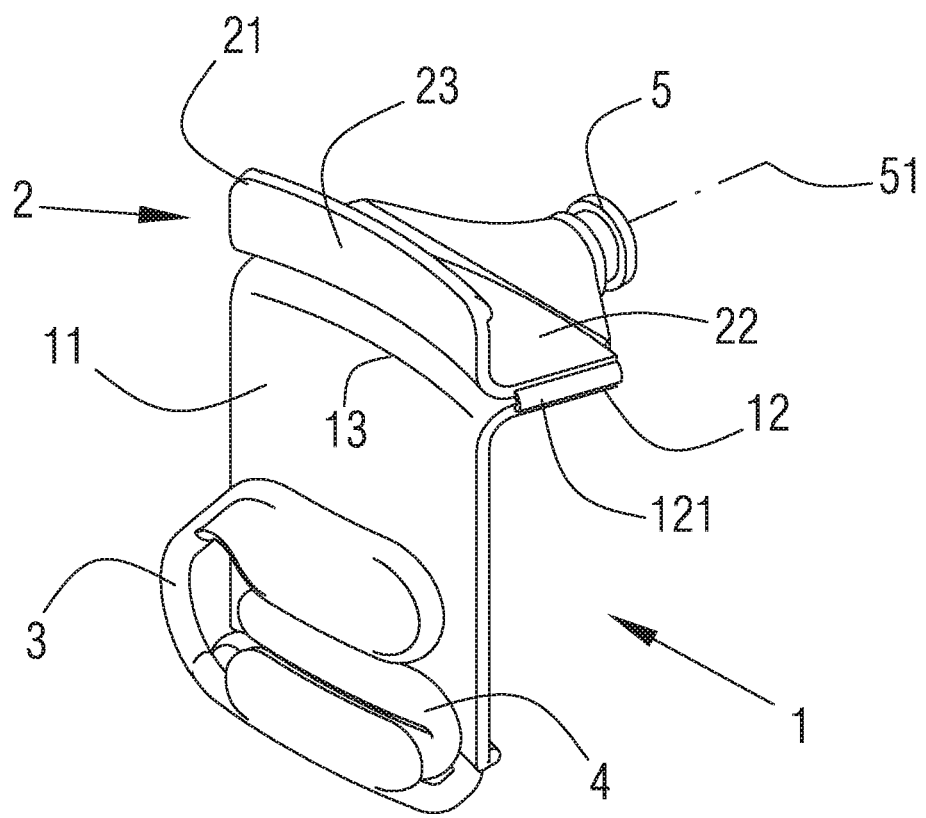

As is also schematically depicted in the FIGS. 4, 5 and 6, the same joint of the fin 2 with the smaller base 12 is implemented such that in another position of the same joint, the same side 22 of the L profile 21, which was previously the continuation of the same smaller planar base 12 of the baseband 1, is now positioned in contact and on the same smaller base 12 of the baseband 1.

The edge 111 or end of the larger base 11 which is in the position opposite the intersection line 13 with the smaller base 12 incorporates two arms 3, 4 which are each articulated with respect to the larger base 11 itself.

In one position of the joint thereof schematically depicted in FIGS. 4, 5 and 6, the arms 3, 4 are positioned and folded on the face of the larger base 11 which corresponds to the concave part of the same larger base 11.

In another position of the same joint schematically depicted in FIGS. 1, 2 and 3, the same arms 3, 4 are arranged extended and with an orientation perpendicular to the larger base 11 itself, in the direction opposite the position of the smaller base 12.

In addition to what has been previously explained, the edge 122 of the smaller base 12, which is in a position opposite the intersection line 13 with the larger base 11, incorporates a tubular extension 5 towards the exterior of the smaller base 12 itself in this preferred embodiment with the axial axis 51 thereof contained in the same plane as the smaller base 12 and in a direction perpendicular to the larger base 11.

Figure 7:
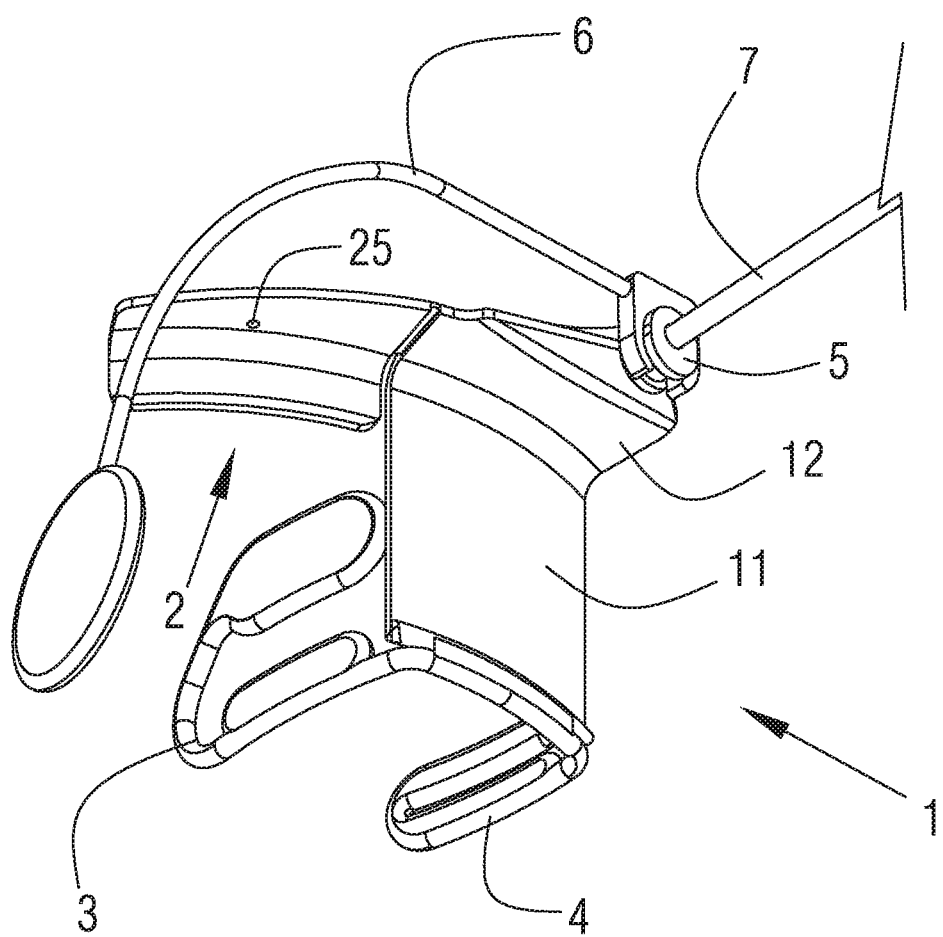
FIGS. 7 and 8 are perspective and schematic views of a preferred embodiment of the cardiac surgery retractor of the present invention with the accessory carrying the diaphragm incorporated.
Figure 8:
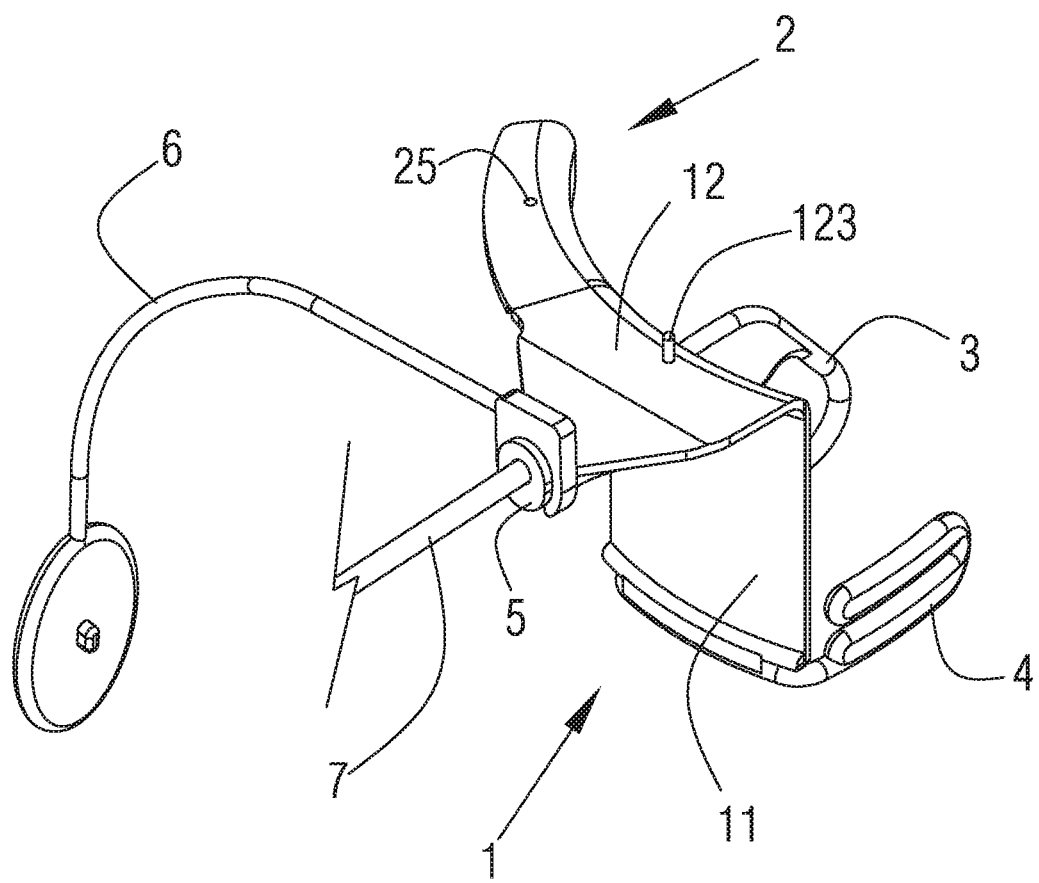
Figure 9:
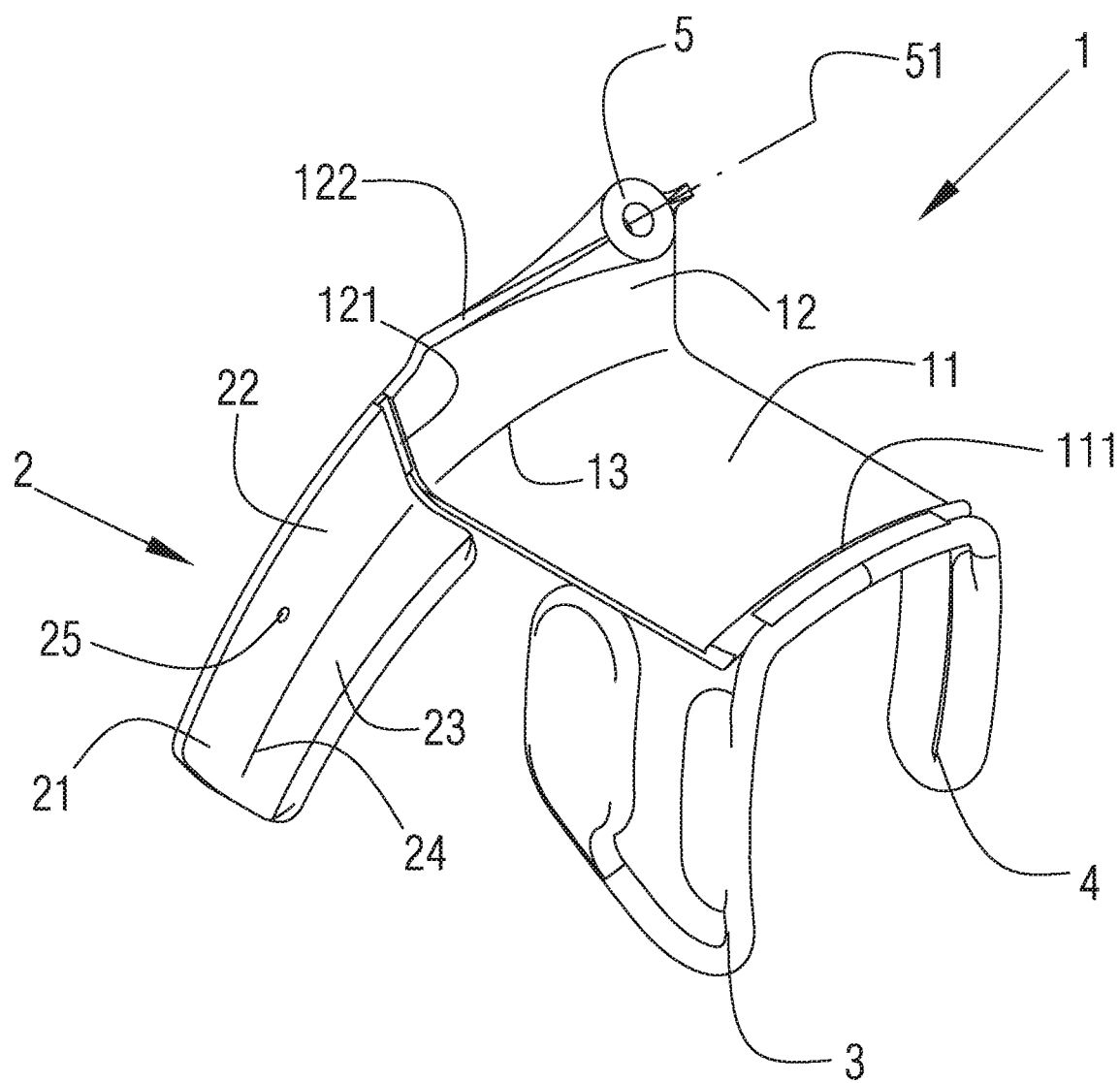
FIGS. 9, 10 and 11 are perspective and schematic views of another preferred embodiment of the cardiac surgery retractor of the present invention with the joint thereof unfolded.
Figure 10:
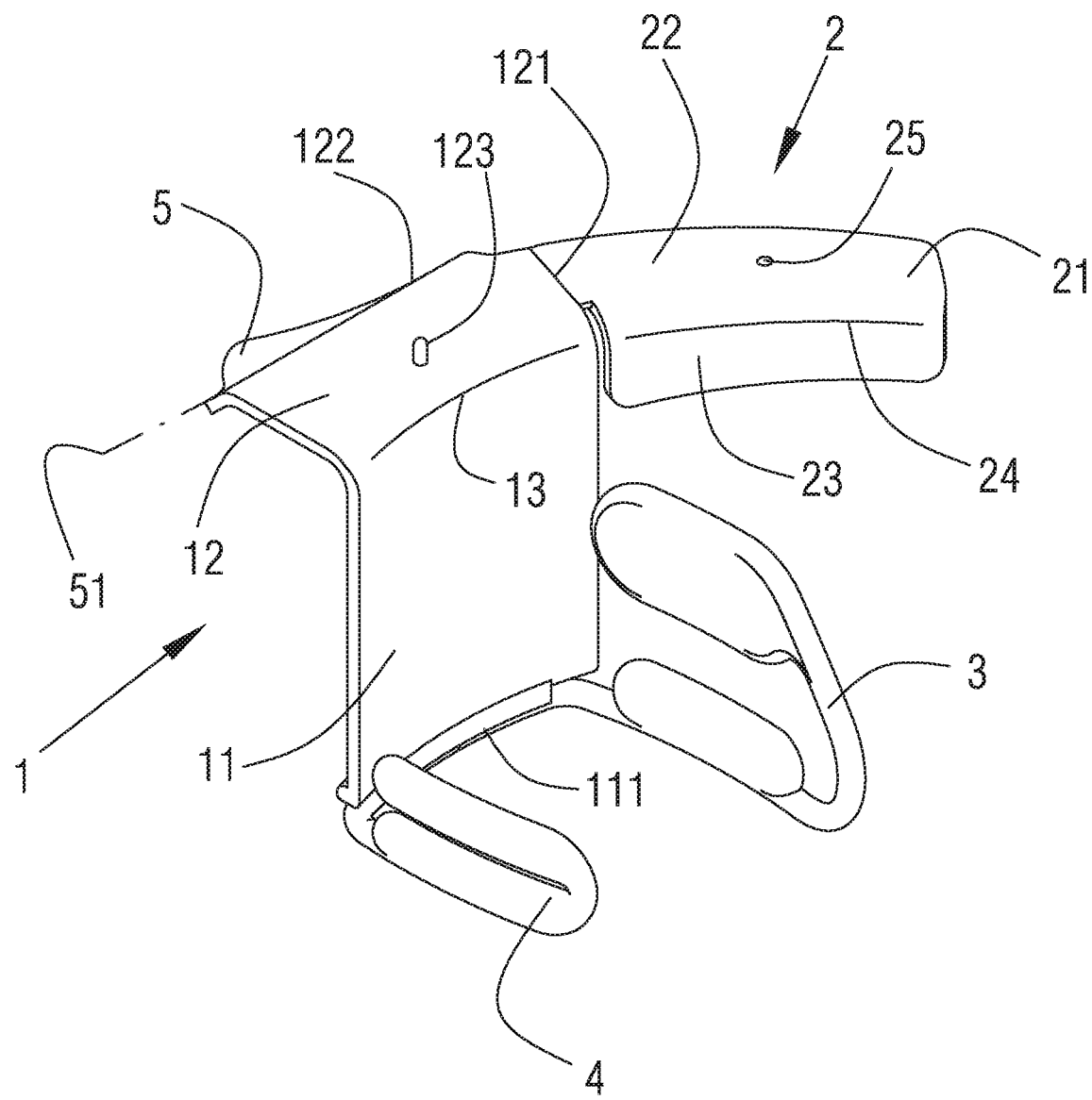
Figure 11:
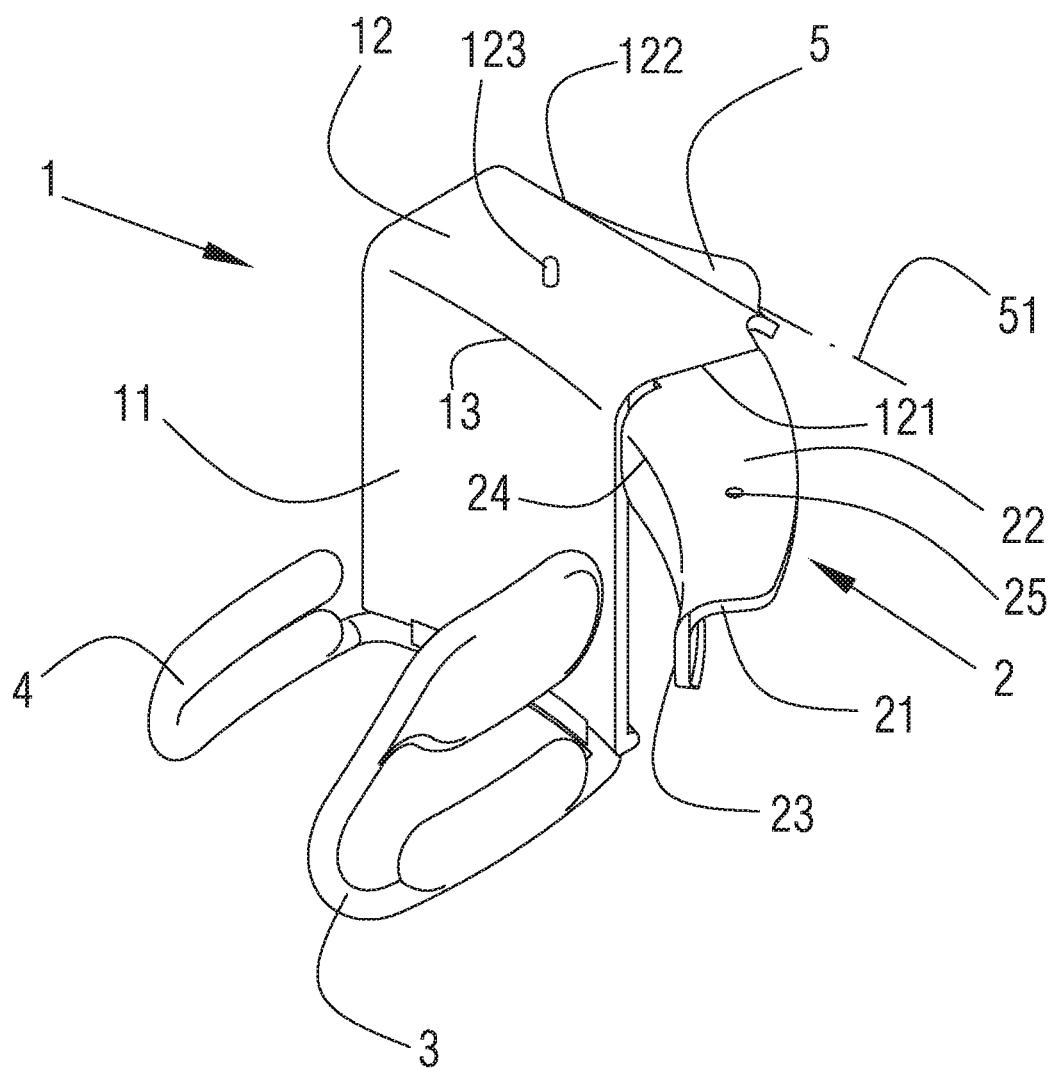
Figure 12:
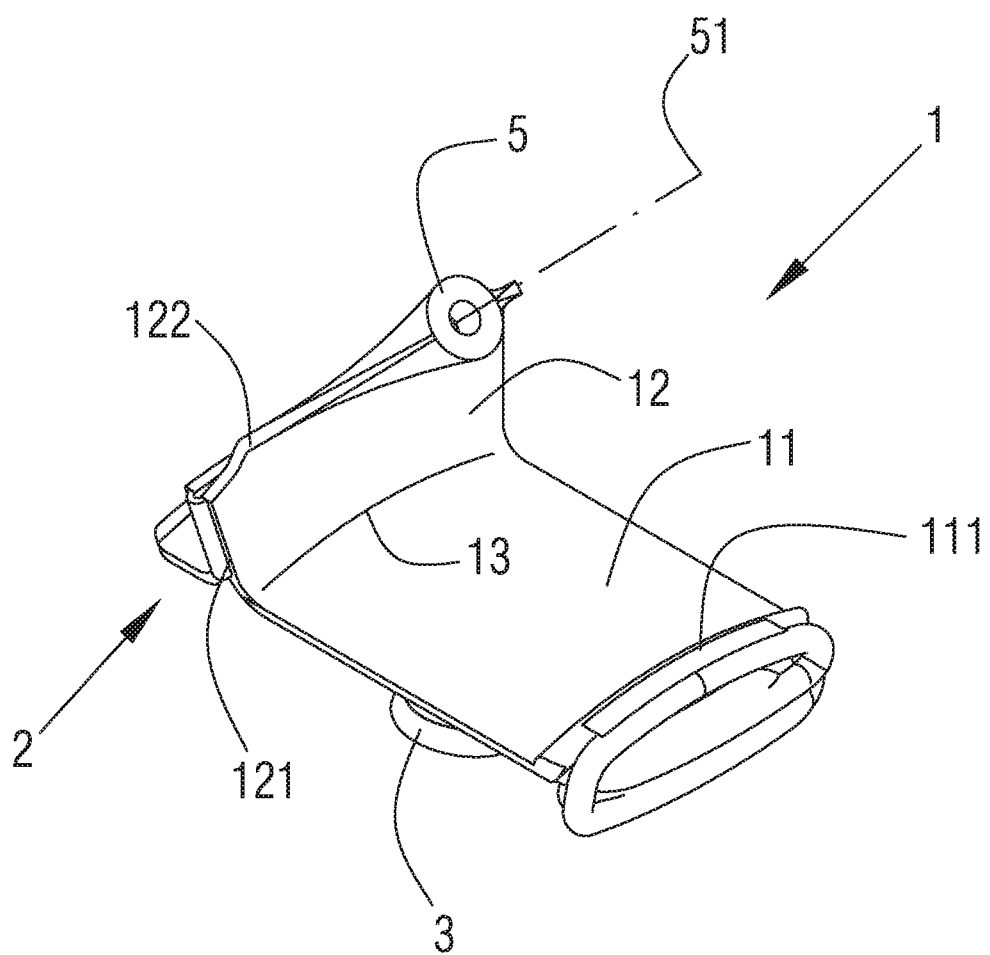
FIGS. 12, 13 and 14 are perspective and schematic views of the preferred embodiment of the cardiac surgery retractor of the present invention of FIGS. 9 to 11, but with the joint thereof folded.
Figure 13:
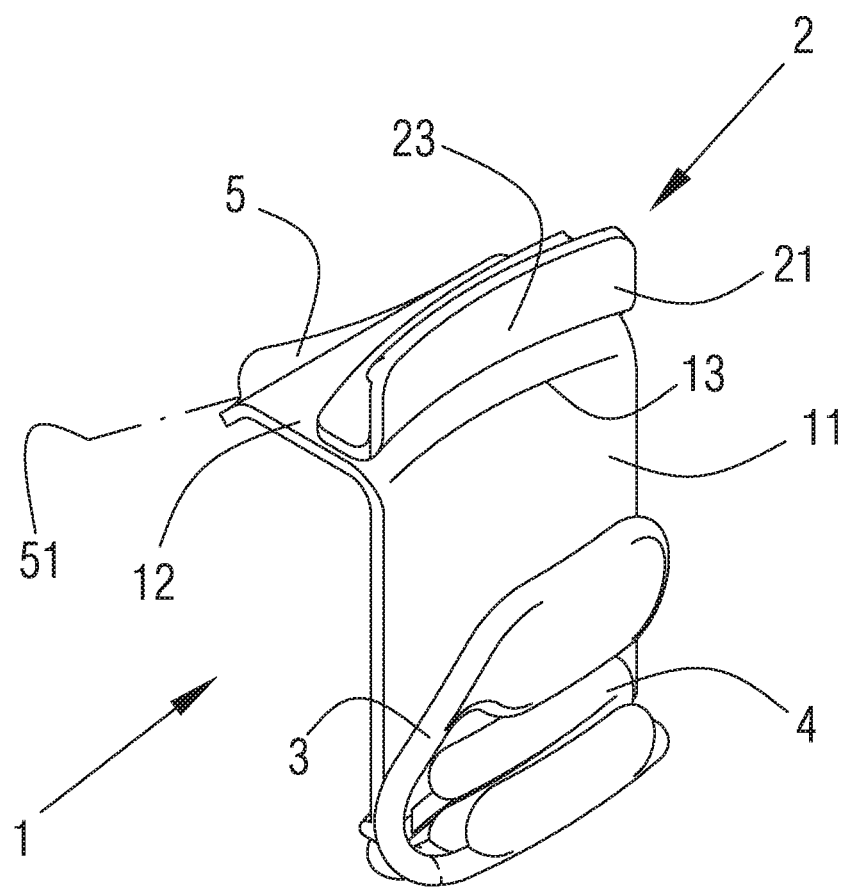
Figure 14:
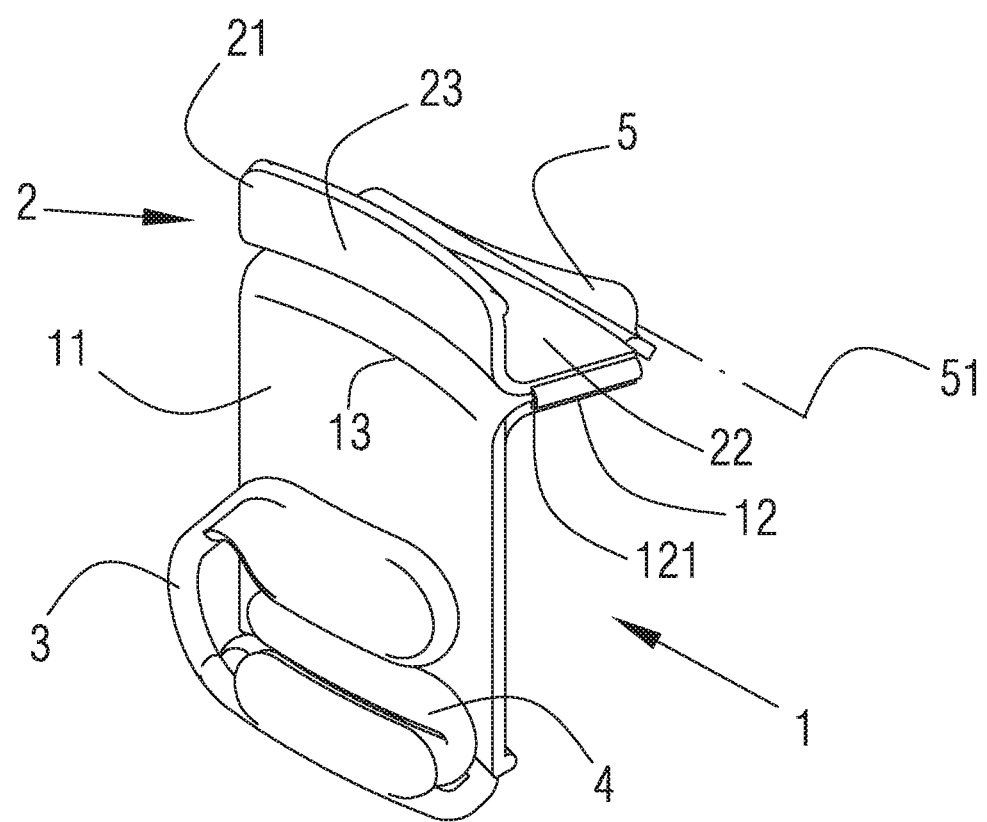

The tubular extension 5 is enabled for carrying an accessory 6 carrying a diaphragm in a manner already known in the state of the art, like the one depicted in FIGS. 7 and 8 for example.

In FIGS. 7 and 8, it appears schematically depicted how the accessory 6 carrying a diaphragm is installed in the tubular extension 5 and which is preferably used in the case of MIS cardiac surgery.

The cardiac surgery retractor of the invention also incorporates fixing means for fixing the position of the joint and positioning the fin 2 on the smaller base 12 of the baseband 1, as is depicted in FIGS. 4, 5 and 6.

In the preferred embodiment, the fixing means comprise a hole 25 in the planar side 22 of the L profile 21 of the fin 2 which is complementary to an awl 123 positioned in the smaller base 12 of the baseband 1.

When the fin 2 is positioned on the baseband 12, as is depicted in FIGS. 4, 5 and 6, the awl 123 is introduced into the hole 25, thus fixing the fin 2 in said position.

In general, the preferred embodiment of the cardiac surgery retractor of the present invention depicted in FIGS. 1 to 6 with the axial axis 51 of the tubular extension contained in the same plane as the smaller base 12 will preferably be used in minimally invasive cardiac surgery (MIS).

In another preferred embodiment schematically depicted in the FIGS. 9 to 14, the tubular extension 5 has the axial axis 51 contained in a plane oblique with respect to the smaller planar base 12 and more specifically with an angle of 45 degrees.

Figure 15:
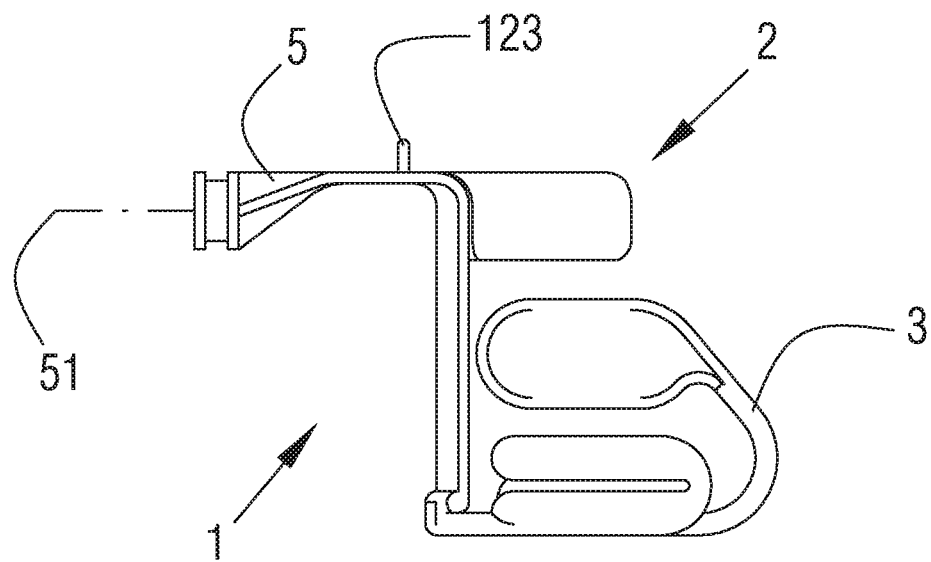
FIG. 15 is a schematic and comparative view of two preferred embodiments of the cardiac surgery retractor of the present invention.
Figure 15:
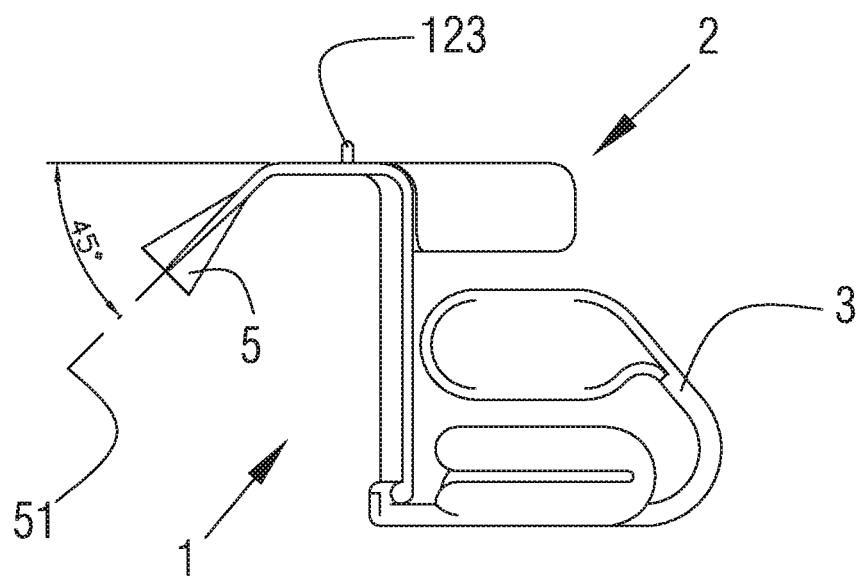

In FIG. 15, both preferred embodiments appear comparatively in an elevation view in order to thus observe with greater clarity the difference between both in relation to the different inclination of the tubular extension 5 with respect to the smaller band 12.

As is also depicted in FIGS. 7 and 8, the tubular extension 5 is also enabled for incorporating a handle 7 inserted coaxially to the axial axis 51 during the use of the cardiac surgery retractor of the invention.

In general, the preferred embodiment of the cardiac surgery retractor of the present invention depicted in FIGS. 9 to 14 with the axial axis 51 of the tubular extension 5 contained in a plane which forms an angle of 45° with respect to the smaller base 12 will preferably be used in conventional cardiac surgery.

The cardiac surgery retractor of the present invention is a very useful and novel device both for conventional mitral cardiac surgery and for minimally invasive cardiac surgery (MIS) since it provides improved and complete exposure of the mitral valve and its ring from the interior of the left auricle.

The cardiac surgery retractor of the invention is a truly versatile system due to the adaptability of the fin 2 thereof and the arms 3, 4 thereof and the different joints thereof described allowing the effective adaptability thereof to each situation and/or patient.

The cardiac surgery retractor of the invention is designed for being inserted in a folded or closed position (as depicted in FIGS. 4, 5 and 6 or 12, 13 and 14) by means of holding it with a clamp at the protrusion which supports the fin 2 in the closed position.

Once the left auricle is open wide, the cardiac surgery retractor of the invention is introduced inside the left auricle cavity and then (as is depicted in FIGS. 1, 2 and 3 or 9, 10 and 11), the lateral fin 2 is completely opened to provide an anterocaudal separation and the arms 3, 4 are opened and extended to the desired position to expose the caudal part (right) and cranial part (left) of the mitral valve and the mitral ring, thus replacing the valves of the sternal retractor by means of which the exposure and therefore the work of the surgeon is greatly improved.

In MIS surgery, the visualization of the specific components of the mitral valve, for example the posteromedial papillary muscle may require additional maneuvers whereby it is necessary to hold the diaphragm. To this end, the cardiac surgery retractor of the invention has an accessory 6 so that this action is atraumatic.

Once the intervention has been concluded, the lateral arms 3, 4 are folded again as is depicted in FIGS. 4, 5 and 6 or 12, 13 and 14.

The cardiac surgery retractor of the present invention has significant advantages since it is easily mountable, removable and disposable and can be used both in conventional mitral valve surgery and in MIS.

In the use thereof, the cavity of the left auricle opens from within and close to the mitral valve and thus better exposes the mitral valve and creates less difficulty for the surgeon.

It has two arms 3, 4 for exposing both the caudal part (right) of the mitral valve and its ring as well as the cranial part (left).

The arms 3, 4 are malleable, displaceable and expandable in order to thus be adapted to the internal walls of the left auricle and one of these provides an additional function in order to separate an internal structure or tense the sutures used in mitral valve replacement or in mitral annuloplasty.

The cardiac surgery retractor of the invention has a foldable fin 2 which, in the folded position, is used for holding and being introduced inside the left auricle and in the open position exerts anterocaudal traction, replacing the other fenestrated valve of the sternal retractor and thus offers a more accessible space for the surgeon.

In addition, a disposable accessory, which is easy to mount, can be used for caudally displacing the diaphragm and improving the field of vision of the surgeon and thus avoiding the need to separate the diaphragm with a stitch which can sometimes be severely traumatic.

The details, the shapes, the dimensions and other accessory elements as well as the materials used in the manufacture of the cardiac surgery retractor of the invention can be conveniently substituted for others which are technically equivalent and do not depart from the essentiality of the invention or from the scope defined by the claims which are included below.

What is claimed is:

1. A cardiac surgery retractor configured for use in a minimally invasive surgery and for the use thereof with a diaphragm, characterized by the fact that the retractor comprises a baseband (1) formed by a first base (11) and a second base (12), the first base (11) and the second base (12) mutually arranged in a perpendicular manner and forming a cross-section of the baseband (1) in the shape of an L, the second base (12) being planar and the first base (11) having a curved geometry with a convex surface in relation to the contact thereof with the second base (12) and the baseband (1) therefore having an intersection line (13) between the first base (11) and the second base (12) with a geometric shape of a circumferential arc; the baseband (1) incorporating a fin (2) having a profile (21) with a cross-section also in the shape of an L and the fin (2) being articulated at the second base (12) of the baseband (1) and more specifically articulated at a lateral edge (121) of the second base (12) contiguous to the contact thereof with the first base (11); such that in one position of a joint of the fin (2), one side (22) of the L profile (21) forming the fin (2) is the continuation of the same second planar base (12) of the baseband (1) and the other side (23) of the same L profile (21) of the fin (2) is the continuation of the curved geometry of the first base (11) of the baseband (1) and a line of a vertex (24) of the L profile (21) is the continuation of the geometric shape of the intersection line (13) between the first base (11) and the second base (12) of the baseband (1); and in another position of the joint of the fin (2), the side (22) of the L profile (21) of the fin (2) is positioned on the second base (12) of the baseband (1); the surface of the convex face of the first base (11) and the side (23) of the L profile (21) of the fin (2) both being rough; and an end of the first base (11) opposite the intersection line (13) with the second base (12) incorporates two arms (3, 4) articulated with respect to the first base (11) itself which, in one position of said joint of the arms (3, 4), are positioned on the face of the first base (11) which corresponds to a concave part of the first base (11) and in another position of the same joint are arranged extended and with an orientation perpendicular to the same first base (11) in a direction opposite the position of the second base (12); a edge (122) of the second base (12), which is in a position opposite the intersection line (13) with the first base (11), incorporating a tubular extension (5) towards the exterior of the second base (12).

2. The cardiac surgery retractor according to claim 1, wherein that the tubular extension (5) is enabled for carrying an accessory (6) carrying a diaphragm.

3. The cardiac surgery retractor according to claim 1, wherein that the retractor incorporates fixing means for positioning the side (22) of the L profile (21) of the fin (2) on the second base (12) of the baseband (1).

4. The cardiac surgery retractor according to claim 3, wherein that the fixing means comprise a hole (25) in the same planar side (22) of the L profile (21) of the fin (2) which is complementary to an awl (123) positioned on the second base (12) of the baseband (1).

5. The cardiac surgery retractor according to claim 1, characterized by the fact wherein that a axial axis (51) of the tubular extension (5) is contained in a same plane which contains the second base (12).

6. The cardiac surgery retractor according to claim 1, wherein that a axial axis (51) of the tubular extension (5) is contained in an oblique plane with respect to the second base (12).

7. The cardiac surgery retractor according to claim 6, wherein that the oblique plane, which contains the axial axis (51) of the tubular extension (5), forms an angle of 45° with respect to the second base (12).

8. The cardiac surgery retractor according to claim 1, wherein that the arms (3, 4) are malleable.

9. The cardiac surgery retractor according to claim 1, wherein that the tubular extension (5) is enabled for incorporating a handle (7) inserted coaxially to a axial axis (51) of the tubular extension (5).

* * * * *

UNITED STATES PATENT AND TRADEMARK OFFICE
CERTIFICATE OF CORRECTION

| | | |
|---|---|---|
| PATENT NO. | : 10,517,581 B2 | Page 1 of 1 |
| APPLICATION NO. | : 15/739728 | |
| DATED | : December 31, 2019 | |
| INVENTOR(S) | : Anas Sarraj Asil | |

It is certified that error appears in the above-identified patent and that said Letters Patent is hereby corrected as shown below:

On the Title Page

Item [30], delete "201531065" and insert -- P201531065 --

Signed and Sealed this
Third Day of March, 2020

Andrei Iancu
*Director of the United States Patent and Trademark Office*